United States Patent
Kawashima

(10) Patent No.: US 9,864,106 B2
(45) Date of Patent: Jan. 9, 2018

(54) SEMICONDUCTOR DBR, SEMICONDUCTOR LIGHT-EMITTING DEVICE, SOLID-STATE LASER, PHOTOACOUSTIC APPARATUS, IMAGE-FORMING APPARATUS, AND METHOD FOR MANUFACTURING SEMICONDUCTOR DBR

(71) Applicant: CANON KABUSHIKI KAISHA, Tokyo (JP)

(72) Inventor: Takeshi Kawashima, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 447 days.

(21) Appl. No.: 14/307,328

(22) Filed: Jun. 17, 2014

(65) Prior Publication Data

US 2014/0377459 A1   Dec. 25, 2014

(30) Foreign Application Priority Data

Jun. 19, 2013 (JP) ................. 2013-128283

(51) Int. Cl.
  *H01L 33/10* (2010.01)
  *G02B 1/10* (2015.01)
  (Continued)

(52) U.S. Cl.
  CPC .......... *G02B 1/105* (2013.01); *G01N 21/1702* (2013.01); *G03G 15/04072* (2013.01); *H01L 33/105* (2013.01); *H01S 5/187* (2013.01); *H01S 5/18358* (2013.01); *H01S 5/18361* (2013.01); *H01L 33/10* (2013.01); *H01L 33/46* (2013.01);
  (Continued)

(58) Field of Classification Search
  CPC ....... H01L 33/32; H01L 33/10; H01L 33/105; H01L 33/46; H01L 51/5265
  See application file for complete search history.

(56) References Cited

U.S. PATENT DOCUMENTS 5,977,612 A * 11/1999 Bour .............. B82Y 20/00
                                                      257/103
6,597,017 B1   7/2003 Seko
(Continued)

FOREIGN PATENT DOCUMENTS

CN   101257080 A   9/2008
CN   101478115 A   7/2009
(Continued)

*Primary Examiner* — Matthew Song
(74) *Attorney, Agent, or Firm* — Canon U.S.A. Inc., IP Division

(57) ABSTRACT

A semiconductor distributed Bragg reflector (DBR) including a first multilayer structure including a plurality of first semiconductor layers and one or more second semiconductor layers each interposed between a corresponding pair of the plurality of first semiconductor layers; a second multilayer structure including a plurality of third semiconductor layers and one or more second semiconductor layers each interposed between a corresponding pair of the plurality of third semiconductor layers; and a protection layer interposed between the first multilayer structure and the second multilayer structure. The second semiconductor layer has a lower decomposition temperature than the first semiconductor layer. The third semiconductor layer has a lower decomposition temperature than the second semiconductor layer.

15 Claims, 11 Drawing Sheets

(51) Int. Cl.
*G01N 21/17* (2006.01)
*G03G 15/04* (2006.01)
*H01S 5/187* (2006.01)
*H01L 51/52* (2006.01)
*H01L 33/46* (2010.01)
*H01S 3/0941* (2006.01)
*H01S 5/183* (2006.01)
*H01S 5/32* (2006.01)
*H01S 5/343* (2006.01)
*H01S 5/42* (2006.01)
*H01S 3/16* (2006.01)
*H01S 5/30* (2006.01)

(52) U.S. Cl.
CPC ......... *H01L 51/5265* (2013.01); *H01S 3/0941* (2013.01); *H01S 3/1633* (2013.01); *H01S 5/18308* (2013.01); *H01S 5/3063* (2013.01); *H01S 5/3201* (2013.01); *H01S 5/34333* (2013.01); *H01S 5/423* (2013.01); *H01S 2304/04* (2013.01)

(56) References Cited

U.S. PATENT DOCUMENTS

| | | | |
|---|---|---|---|
| 2004/0104398 A1* | 6/2004 | Hon | H01L 33/105 257/98 |
| 2009/0213889 A1 | 8/2009 | Takeuchi | |
| 2010/0224892 A1* | 9/2010 | Nakahara | H01L 33/10 257/98 |
| 2013/0070802 A1* | 3/2013 | Ichihara | H01S 3/091 372/70 |

FOREIGN PATENT DOCUMENTS

| | | |
|---|---|---|
| CN | 102525550 A | 7/2012 |
| CN | 103034082 A | 4/2013 |
| EP | 19556664 A1 | 8/2008 |
| JP | 2000-349393 A | 12/2000 |
| JP | 2001-094208 A | 4/2001 |
| JP | 2013-171992 A | 9/2013 |

* cited by examiner

SEMICONDUCTOR DBR, SEMICONDUCTOR LIGHT-EMITTING DEVICE, SOLID-STATE LASER, PHOTOACOUSTIC APPARATUS, IMAGE-FORMING APPARATUS, AND METHOD FOR MANUFACTURING SEMICONDUCTOR DBR

BACKGROUND OF THE INVENTION

Field of the Invention

The present invention relates to a semiconductor DBR, a semiconductor light-emitting device, a solid-state laser, a photoacoustic apparatus, an image-forming apparatus, and a method for manufacturing the semiconductor DBR.

Description of the Related Art

A vertical-cavity-type surface emitting laser (vertical cavity surface emitting laser, VCSEL) is a laser including a cavity formed on a substrate in the vertical direction of the laser, the cavity being constituted by two reflectors and an active layer interposed between the two reflectors. As a reflector, a Bragg reflector (distributed Bragg reflector, DBR) including two layers having different refractive indices, the two layers being alternately stacked on top of one another a plurality of times and each layer having an optical thickness corresponding to ¼ wavelength, is used. The layers constituting a DBR are composed of a dielectric substance or a semiconductor and, in many cases, a semiconductor is employed from the viewpoint of formation of a device.

The thickness of an active layer of a VCSEL is very small, which makes it difficult to achieve a large gain. Therefore, the reflectance of reflectors constituting a cavity is desirably increased to 99% or more. In order to increase the reflectance of DBRs that serve as reflectors, the number of the pairs of the two layers having different refractive indices and a difference in the refractive indices are desirably increased.

In the case where a DBR constituted by semiconductors is formed by epitaxial growth, a difference in lattice constant between a substrate and a semiconductor to be epitaxially grown on the substrate is desirably reduced. A large difference in lattice constant causes lattice strain, which causes an in-plane stress in the epitaxial film. This may lead to degradation of the surface smoothness of the semiconductor layer and occurrence of cracking in the semiconductor layer.

For example, a tensile stress occurs in an AlGaN layer formed on a GaN substrate, and a compressive stress occurs in an InGaN layer formed on a GaN substrate. In Japanese Patent Laid-Open No. 2000-349393, a semiconductor DBR is formed on a GaN substrate by alternately growing an AlGaN layer and an InGaN layer on top of one another at 800° C. Thus, in Japanese Patent Laid-Open No. 2000-349393, occurrence of cracking is suppressed by alternately stacking an AlGaN layer and an InGaN layer on top of one another, thereby compensating for lattice strain.

SUMMARY OF THE INVENTION

Accordingly, aspects of the present invention may provide a semiconductor DBR constituted by layers having good crystal quality.

Specifically, aspects of the present invention provide a semiconductor distributed Bragg reflector (DBR) including a first multilayer structure including a plurality of first semiconductor layers and one or more second semiconductor layers each interposed between a corresponding pair of the plurality of first semiconductor layers; a second multilayer structure including a plurality of third semiconductor layers and one or more second semiconductor layers each interposed between a corresponding pair of the plurality of third semiconductor layers; and a protection layer interposed between the first multilayer structure and the second multilayer structure. The second semiconductor layer has a lower decomposition temperature than the first semiconductor layer. The third semiconductor layer has a lower decomposition temperature than the second semiconductor layer. The semiconductor DBR has a peak reflectance at a wavelength $\lambda$. The plurality of first semiconductor layers, the one or more second semiconductor layers, and the plurality of third semiconductor layers each have an optical thickness of $n\lambda/4$ (where n is an odd number of 1 or more). The protection layer has an optical thickness of $m\lambda/2$ (where m is a natural number of 1 or more). A portion of the protection layer at which the protection layer is brought into contact with the second multilayer structure includes a material having a higher decomposition temperature than the third semiconductor layer.

Further features of the present invention will become apparent from the following description of exemplary embodiments with reference to the attached drawings.

DESCRIPTION OF THE EMBODIMENTS

Figure 1:
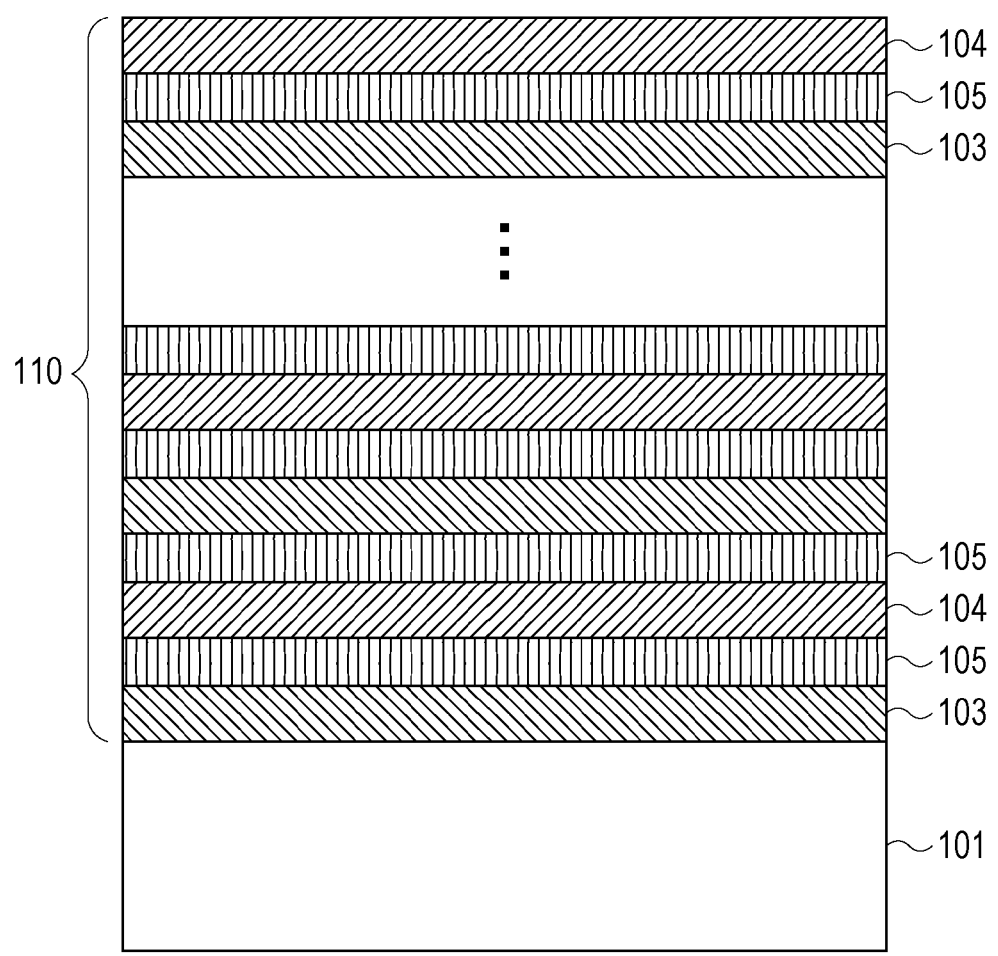
FIG. 1 is a diagram illustrating a structure of a semiconductor DBR according to an embodiment of the present invention.

As described above, in Japanese Patent Laid-Open No. 2000-349393, an AlGaN layer and an InGaN layer are alternately grown on top of one another at 800° C. However, AlGaN and InGaN have different optimal growth temperatures. Specifically, AlGaN is preferably grown at about 1,000° C. to about 1,300° C., and InGaN is preferably grown at about 600° C. to about 900° C. Accordingly, it is preferable to grow these layers by changing a growth temperature in order to realize a DBR having good crystallinity and a steep heterointerface between the AlGaN layer and the InGaN layer, that is, a DBR having a high reflectance.

However, changing of a growth temperature may cause degradation of crystal quality. For example, if the temperature is increased to the growth temperature of an AlGaN layer after an InGaN layer is grown, the surface of the InGaN layer is exposed to high heat and consequently the InGaN layer is decomposed, which makes it difficult to grow a flat film. In addition, each time the temperature is increased or reduced, an in-plane stress caused due to a difference in thermal expansion coefficient between the InGaN layer and the AlGaN layer occurs in both the InGaN layer and the AlGaN layer, which increases the risk of the occurrence of crystal defects. In particular, when several tens of periods of an InGaN layer and an AlGaN layer are stacked on top of one another in order to increase the reflectance of a DBR, the temperature is increased and reduced repeatedly several tens of times. As a result, several tens of thermal histories are accumulated. The above factors lead to degradation of the crystal quality of a semiconductor DBR, which results in a reduction in the reflectance of the semiconductor DBR.

If such a semiconductor DBR having degraded crystal quality is used for manufacturing a light-emitting device such as a VCSEL, the light emitting property of the light-emitting device becomes degraded.

Accordingly, the present invention provides a semiconductor DBR including a layer having a lower refractive index and a layer having a higher refractive index that have different growth temperatures, such as a semiconductor DBR including an AlGaN layer and an InGaN layer, in which thermal decomposition of the layers is suppressed. The present invention also provides a semiconductor DBR in which a thermal history due to changing of a growth temperature is reduced. Since the above-described semiconductor DBR has good crystal quality, it serves as a reflector having a high reflectance.

A semiconductor DBR according to an embodiment of the present invention is described below with reference to the attached drawings. The following description in this embodiment is given taking a semiconductor DBR including GaN-based materials as an example. However, semiconductor materials that can be employed in this embodiment are not limited to these; in addition to GaN-based materials, semiconductor materials such as InP-based materials and GaAs-based materials may also be employed.

Structure

FIG. 1 shows a semiconductor DBR 110 according to the embodiment, which is formed on a substrate 101. The semiconductor DBR according to the embodiment includes an AlGaN/GaN multilayer structure 103 that serves as a first multilayer structure, a phase-matching layer (protection layer) 105, an InGaN/GaN multilayer structure 104 that serves as a second multilayer structure, and a phase-matching layer 105, which are stacked on top of one another repeatedly in this order. The semiconductor DBR 110 according to the embodiment is designed so that a wavelength λ at which a peak reflectance occurs (hereinafter, also referred to as "peak wavelength") is about 400 nm. The semiconductor DBR according to the embodiment may be designed so as to correspond to any peak wavelength.

Alternatively, the InGaN/GaN multilayer structure 104, the phase-matching layer 105, the AlGaN/GaN multilayer structure 103, and the phase-matching layer 105 of the semiconductor DBR 110 may be stacked on top of one another in this order.

In this embodiment, a GaN-based material is grown on the substrate 101. Therefore, the material of the substrate 101 is desirably a material having a lattice constant close to that of GaN. Examples of a substrate that may be used as the substrate 101 include a GaN substrate and a GaN template substrate formed by depositing a GaN layer on a substrate other than GaN, which is composed of sapphire, Si, GaAs, SiC, or the like and on which GaN can be grown. The material of the substrate 101 is selected appropriately depending on a material to be grown on the substrate 101.

Figure 2:
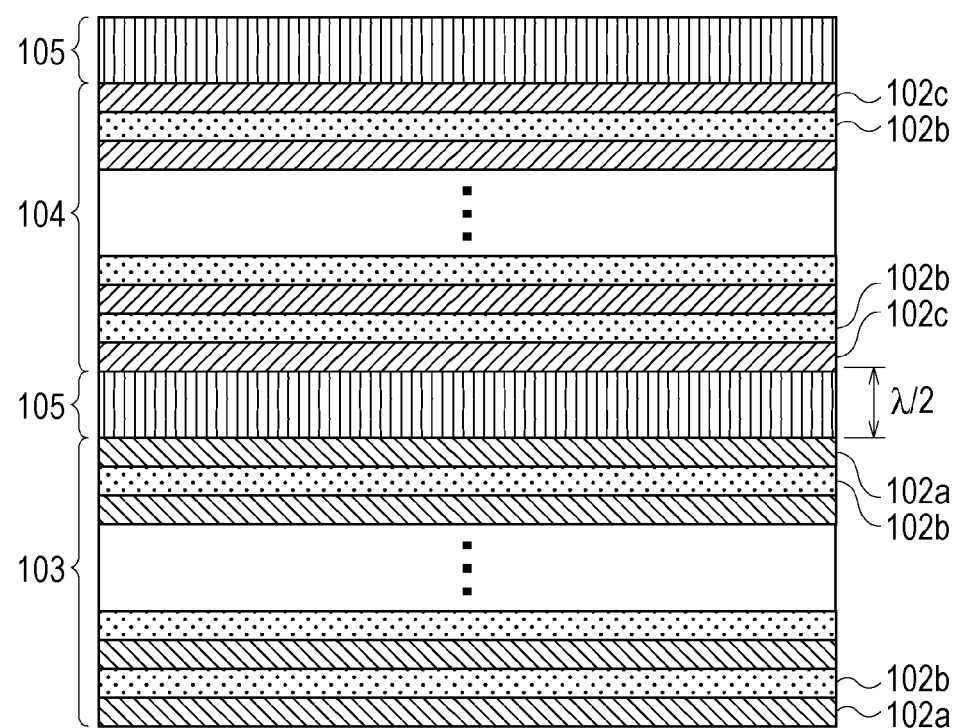
FIG. 2 is a diagram illustrating a detailed structure of a semiconductor DBR according to an embodiment of the present invention.

FIG. 2 illustrates detailed structures of the AlGaN/GaN multilayer structure 103, the InGaN/GaN multilayer structure 104, and the phase-matching layer 105.

The AlGaN/GaN multilayer structure 103 includes AlGaN layers 102a that serve as first semiconductor layers and that each have an optical thickness of λ/4 and GaN layers 102b that serve as second semiconductor layers and that each have an optical thickness of λ/4. The GaN layers 102b are each interposed between the corresponding pair of the AlGaN layers 102a. In this embodiment, the optical thickness of a layer refers to the product of the thickness of the layer and the refractive index of the layer.

The InGaN/GaN multilayer structure 104 includes the GaN layers 102b and InGaN layers 102c that serve as third semiconductor layers and that each have an optical thickness of λ/4. The GaN layers 102b are each interposed between the corresponding pair of the InGaN layers 102c. Note that the optical thicknesses of the layers constituting the AlGaN/GaN multilayer structure 103 and the InGaN/GaN multilayer structure 104 are not limited to λ/4 and may be alternatively set to nλ/4, where n is an odd number of 1 or more and is preferably 1 or 3.

The phase-matching layer 105 has an optical thickness of λ/2 and is interposed between the AlGaN/GaN multilayer structure 103 and the InGaN/GaN multilayer structure 104. The phase-matching layer 105 serves to match the phase of a standing wave between the AlGaN/GaN multilayer structure 103 and the InGaN/GaN multilayer structure 104. In this embodiment, the phase-matching layer 105 is a monolayer composed of GaN and is in contact with the AlGaN layer 102a of the AlGaN/GaN multilayer structure 103 and the InGaN layer 102c of the InGaN/GaN multilayer structure 104. The optical thickness of the phase-matching layer 105 is not limited to λ/2 and may be alternatively set to mλ/2, where m is a natural number of 1 or more and is preferably 1 or 2.

Refractive Index

Generally, the following relationship exists among the refractive indices of the AlGaN layer 102a, the GaN layer 102b, and the InGaN layer 102c:

InGaN layer 102c>GaN layer 102b>AlGaN layer 102a

In other words, in the AlGaN/GaN multilayer structure 103, the AlGaN layer 102a serves as a layer having a lower refractive index, and the GaN layer 102b serves as a layer having a higher refractive index. On the other hand, in the InGaN/GaN multilayer structure 104, the GaN layer serves as a layer having a lower refractive index, and the InGaN layer serves as a layer having a higher refractive index.

A portion of the phase-matching layer 105 which is in contact with the interface between the phase-matching layer 105 and the AlGaN layer 102a and which has an optical thickness of λ/4 serves as a layer having a higher refractive index than the AlGaN layer 102a. On the other hand, a portion of the phase-matching layer 105 which is in contact with the interface between the phase-matching layer 105 and the InGaN layer 102c and which has an optical thickness of λ/4 serves as a layer having a lower refractive index than the InGaN layer 102c.

The semiconductor DBR 110 according to the embodiment serves as a DBR because the above-described relationship of refractive index exists.

The semiconductor DBR 110 according to the embodiment serves as a DBR as long as the above relationship exists among the average refractive indices of the portions of the phase-matching layer 105 which are in contact with the respective interfaces and which have an optical thickness of λ/4.

Decomposition Temperature

The larger the band gap of a semiconductor, the higher the decomposition temperature of the semiconductor. For example, the following relationship exists among the decomposition temperatures of nitride semiconductors:

AlN>AlGaN>GaN>InGaN>InN

In other words, in this embodiment, the GaN layer 102b has a lower decomposition temperature than the AlGaN layer 102a. The InGaN layer 102c has a lower decomposition temperature than the AlGaN layer 102a and the GaN layer 102b. In summary, the decomposition temperatures of the layers constituting the semiconductor DBR 110 according to the embodiment satisfy the following relationship:

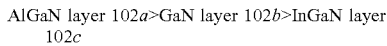

AlGaN layer 102a>GaN layer 102b>InGaN layer 102c

Generally, the above materials have their own optimal growth temperatures. For example, in the case where MOCVD is employed, the AlGaN layer 102a is preferably grown generally at 1,000° C. or more and 1,300° C. or less, which varies depending on the Al content. If the temperature exceeds 1,300° C., which is the decomposition temperature of AlGaN, AlGaN is likely to be decomposed.

The GaN layer 102b is preferably grown at 800° C. or more and 1,200° C. or less. If the temperature exceeds 1,200° C., which is the decomposition temperature of GaN, GaN is likely to be decomposed.

The InGaN layer 102c is preferably grown at 600° C. or more and 900° C. or less, which varies depending on the In content. If the temperature exceeds 900° C., which is the decomposition temperature of InGaN, InGaN is likely to be decomposed.

Both decomposition and supply of semiconductor molecules occur at around the optimal growth temperature. A crystal is allowed to grow because the number of molecules supplied is greater than the number of molecules decomposed. In addition, migration of atoms is active at the optimal growth temperature, which results in good quality and good surface smoothness of a crystal. A temperature close to the upper limit of the optimal growth temperature is the most suitable for growth of a crystal. Therefore, the layers constituting the semiconductor DBR 110 according to the embodiment are preferably grown at a temperature close to the upper limit of the optimal growth temperature.

However, if a growth temperature exceeds the optimal growth temperature, the number of molecules decomposed becomes excessively large and exceeds the number of molecules supplied, which makes it difficult to form a film having good crystallinity. Thus, in this embodiment, the term "decomposition temperature" refers to the upper limit of the optimal growth temperature. More exactly, a temperature which is higher than the optimal growth temperature and at which the number of semiconductor atoms or semiconductor molecules decomposed exceeds the number of semiconductor atoms or semiconductor molecules supplied may be referred to as "decomposition temperature".

If a semiconductor is grown at a temperature lower than its optimal growth temperature, the number of semiconductor atoms or semiconductor molecules decomposed is reduced. However, migration of atoms becomes weak, which consequently deteriorates the surface smoothness of a crystal.

Methods for forming the AlGaN/GaN multilayer structure 103 and the InGaN/GaN multilayer structure 104 are described below.

In this embodiment, the AlGaN/GaN multilayer structure 103 is formed by epitaxially growing the AlGaN layers 102a and the GaN layers 102b at a constant growth temperature that is lower than or equal to the decomposition temperature of the GaN layer 102b. The growth temperature may be higher than the decomposition temperature of the InGaN layer 102c. Since the growth temperature is lower than or equal to the decomposition temperature of the GaN layer 102b, it is possible to grow the AlGaN layers 102a and the GaN layers 102b while suppressing decomposition of these layers. Since the multilayer structure is formed at a constant growth temperature, the number of repetition of rise and fall of the temperature caused during formation of layers can be reduced.

In this embodiment, the temperature of the layers is increased by heating a layer serving as a substrate used for epitaxial growth. The temperature is reduced by natural heat dissipation. The temperature is measured with a thermocouple installed in the periphery of the substrate. Note that a method for controlling the temperature is not limited as long as it allows the temperature of the layer serving as a substrate used for epitaxial growth to be controlled.

The AlGaN/GaN multilayer structure 103 is formed by, for example, opening and shutting a valve supplying an Al raw material while a Ga raw material is continuously supplied at 800° C. to 1,200° C., which is the growth temperature of GaN. The AlGaN/GaN multilayer structure 103 is formed at 800° C. to 1,200° C., which is the growth temperature of GaN, because GaN is likely to be decomposed if GaN is grown at around 1,300° C. which is the most suitable for growth of AlGaN. The AlGaN/GaN multilayer structure 103 is more preferably formed at 1,000° C. to 1,200° C., where the optimal growth temperatures of AlGaN and GaN coexist.

The InGaN/GaN multilayer structure 104 is formed by epitaxially growing the GaN layers 102b and the InGaN layers 102c at a constant temperature that is lower than or equal to the decomposition temperature of the InGaN layer 102c. Since the temperature is lower than or equal to the decomposition temperature of the InGaN layer 102c, it is possible to grow the GaN layer 102b and the InGaN layer 102c while suppressing decomposition of these layers. Since the multilayer structure is formed at a constant growth temperature, the number of repetition of rise and fall of the temperature caused during formation of layers can be reduced.

The InGaN/GaN multilayer structure 104 is formed by, for example, opening and shutting a valve supplying an In raw material while a Ga raw material is supplied at 600° C. to 900° C., which is the optimal growth temperature of InGaN. The InGaN/GaN multilayer structure 104 is more preferably formed at 800° C. to 900° C., where the optimal growth temperatures of InGaN and GaN coexist.

A method for forming the AlGaN/GaN multilayer structure 103 subsequent to formation of the InGaN/GaN multilayer structure 104 is described below.

The InGaN/GaN multilayer structure 104 is formed by alternately stacking the GaN layer 102b and the InGaN layer 102c on top of one another at a temperature (e.g., 900° C.) lower than or equal to the decomposition temperature of the InGaN layer 102c. By growing the GaN layers 102b at a temperature that is lower than or equal to the decomposition temperature of the InGaN layer 102c and is close to the decomposition temperature of GaN (1,200° C.), the crystal quality of the GaN layers 102b is enhanced.

Subsequently, the AlGaN/GaN multilayer structure 103 is to be formed at a temperature (e.g., 1,150° C.) close to the decomposition temperature of the GaN layer 102b. However, since the uppermost surface of the InGaN/GaN multilayer structure 104 is the InGaN layer 102c, if the temperature is increased to 1,150° C. with the InGaN layer 102c on the uppermost, the InGaN layer 102c may be decomposed because the temperature exceeds its decomposition temperature (900° C.). Therefore, a protection layer that protects the InGaN layer 102c from being decomposed is desirably formed on the InGaN/GaN multilayer structure 104. The material of the protection layer desirably satisfies the following conditions: the protection layer formed of the material has good crystal quality even when being formed at a temperature lower than or equal to the decomposition temperature of the InGaN layer 102c; and the protection layer has a higher decomposition temperature than the growth temperature of the AlGaN/GaN multilayer structure 103.

In this embodiment, accordingly, a phase-matching layer 105 composed of GaN, which serves as a protection layer, is formed at a temperature (e.g., 900° C.) lower than or equal to the decomposition temperature of the InGaN layer 102c. In this embodiment, as described above, the phase-matching layer 105 having an optical thickness of $\lambda/2$ is formed in order to adjust the phase of a standing wave between the AlGaN/GaN multilayer structure 103 and the InGaN/GaN multilayer structure 104.

Alternatively, after a portion of the phase-matching layer 105 has been grown at a temperature lower than or equal to the decomposition temperature of the InGaN layer 102c, the temperature may be changed and subsequently the remaining portion of the phase-matching layer 105 may be grown. In another case, after the growth of a portion of the phase-matching layer 105, the temperature may be increased to the growth temperature of the AlGaN/GaN multilayer structure 103 and then the remaining portion of the phase-matching layer 105 may be grown. In the case where the phase-matching layer 105 has a multilayer structure, after some sublayers of the phase-matching layer 105 are formed at a temperature lower than or equal to the decomposition temperature of the InGaN layer 102c, the growth temperature may be changed appropriately depending on the materials of the other sublayers constituting the multilayer structure.

As described above, the phase-matching layer 105 serves as a protection layer that suppresses decomposition of the InGaN layer 102c as long as a portion of the phase-matching layer 105 at which the phase-matching layer 105 is brought into contact with the InGaN/GaN multilayer structure 104 is composed of a material having a higher decomposition temperature than the InGaN layer 102c.

By protecting the InGaN layer with a material having a higher decomposition temperature than the InGaN layer 102c so as to prevent the InGaN layer from being subjected to a high temperature, the InGaN layer 102c having good crystal quality can be formed.

The phase-matching layer 105 may have any structure as long as the above-described relationship of refractive index and the above-described relationship of decomposition temperature are satisfied. For example, the phase-matching layer 105 may have a multilayer structure constituted by GaN layers and a layer interposed between the GaN layers.

A method for growing the InGaN/GaN multilayer structure 104 subsequent to formation of the AlGaN/GaN multilayer structure 103 is described below.

The AlGaN/GaN multilayer structure 103 is formed by alternately stacking the AlGaN layer 102a and the GaN layer 102b on top of one another at a temperature (e.g., 1,150° C.) that is lower than or equal to the decomposition temperature of the GaN layer 102b and is higher than the decomposition temperature of the InGaN layer 102c.

While the temperature is kept at 1,150° C., the phase-matching layer 105 composed of GaN having an optical thickness of $\lambda/2$ is formed.

The temperature is reduced to a temperature (e.g., 900° C.) lower than or equal to the decomposition temperature of the InGaN layer 102c. Then, the InGaN/GaN multilayer structure 104 is formed by alternately stacking the InGaN layer 102c and the GaN layer 102b on top of one another at 900° C.

In this embodiment, the AlGaN/GaN multilayer structure 103 and the InGaN/GaN multilayer structure 104 are formed at different constant temperatures, which allows a multilayer structure to be formed with a small number of repetition of rise and fall of the temperature. This realizes a reduction in thermal histories accumulated in the semiconductor DBR 110 according to the embodiment. As a result, a semiconductor DBR having good crystal growth can be provided.

In this embodiment, the inventors of the present invention focused on the following points: the decomposition temperatures of AlGaN, InGaN, and GaN satisfy the relationship of "AlGaN>GaN>InGaN"; there is a temperature range in which the optimal growth temperatures of AlGaN and GaN coexist; and there is a temperature range in which the optimal growth temperatures of InGaN and GaN coexist. On the basis of these findings, the inventors have employed AlGaN, InGaN, and GaN as materials of the semiconductor DBR 110 according to the embodiment. Note that any materials that satisfy the above-described relationships of decomposition temperature and optimal growth temperature may be employed as materials of the semiconductor DBR according to the embodiment.

Relationship Among in-Plane Stress, Critical Layer Thickness, and Cracking

The relationship among the in-plane stress, the critical layer thickness, and occurrence of cracking in a semiconductor DBR is described below.

A tensile strain occurred in an AlGaN layer that is epitaxially grown on a GaN substrate causes a tensile stress. On the other hand, a compressive strain occurred in an InGaN layer causes a compressive stress. Thus, if the in-plane stress caused in an epitaxially grown layer and the thickness thereof are not designed appropriately, cracking and pitting may occur in the epitaxially grown layer, which reduces the reflectance of the layer. Cracking and pitting occur when the product of the in-plane stress and the thickness of a layer exceeds a specific value. In a multilayer structure, cracking and pitting occur when the cumulative value of the products of the in-plane stresses and the thicknesses of the layers constituting the multilayer structure exceeds a specific value. The thickness of a layer with which cracking and pitting occur in the layer is herein referred to as "critical layer thickness".

The semiconductor DBR 110 according to the embodiment includes the AlGaN/GaN multilayer structure 103 and the InGaN/GaN multilayer structure 104, which are alternately stacked on top of one another, thereby compensating for lattice strain.

The strain of a substrate semiconductor layer that is epitaxially grown on the c-plane of a substrate and the stress caused in the c-plane are represented by the following formulae:

$$\varepsilon = \frac{a_s - a_0}{a_0} \quad (1)$$

$$\sigma = \left\{ C_{11} + C_{12} - 2\frac{C_{13}^2}{C_{33}} \right\} \varepsilon \quad (2)$$

$$A = \sum_{i=1}^{x} \sigma_i \cdot h_i \quad (3)$$

In Formula (1), $\varepsilon$ represents a lattice strain; $a_s$ represents a lattice constant when the crystal is distorted; and $a_0$ represents a lattice constant when the crystal is not distorted. In Formula (2), $\sigma$ represents an in-plane stress; and $C_{11}$, $C_{12}$, $C_{13}$, and $C_{33}$ each represent an elastic stiffness constant. A positive $\sigma$ means that a tensile stress occurs in the crystal, and a negative $\sigma$ means that a compressive stress occurs in the crystal. In Formula (3), A represents a cumulative stress, which is the total sum of the products of the in-plane stresses and the thicknesses of the layers constituting a multilayer structure including x layers stacked on top of one another; x represents the total number of stacked layers; $\sigma_i$ represents the in-plane stress of the i-th semiconductor layer; and $h_i$ represents the thickness of the i-th semiconductor layer.

When AlGaN and InGaN are epitaxially grown on a GaN substrate so that the thicknesses of the AlGaN layer and the InGaN layer do not exceed the respective critical thicknesses, the a-axis lattice constants of AlGaN and InGaN are substantially equal to that of GaN. Thus, in this embodiment, the cumulative stress A is calculated by substituting the a-axis lattice constant of GaN to $a_s$ and substituting the lattice constant of an epitaxially grown layer that is not distorted to $a_0$. The elastic stiffness constants are determined using the elastic stiffness constants of GaN and AlN in accordance with Vegard's law.

Table 1 shows elastic stiffness constants for the calculation using Formula (2) in this embodiment.

TABLE 1

|  | GaN | AlN | InN |
| --- | --- | --- | --- |
| C11 (GPa) | 365 | 398 | 271 |
| C12 (GPa) | 135 | 142 | 124 |
| C13 (GPa) | 114 | 112 | 94 |
| C33 (GPa) | 381 | 383 | 200 |

Figure 3:
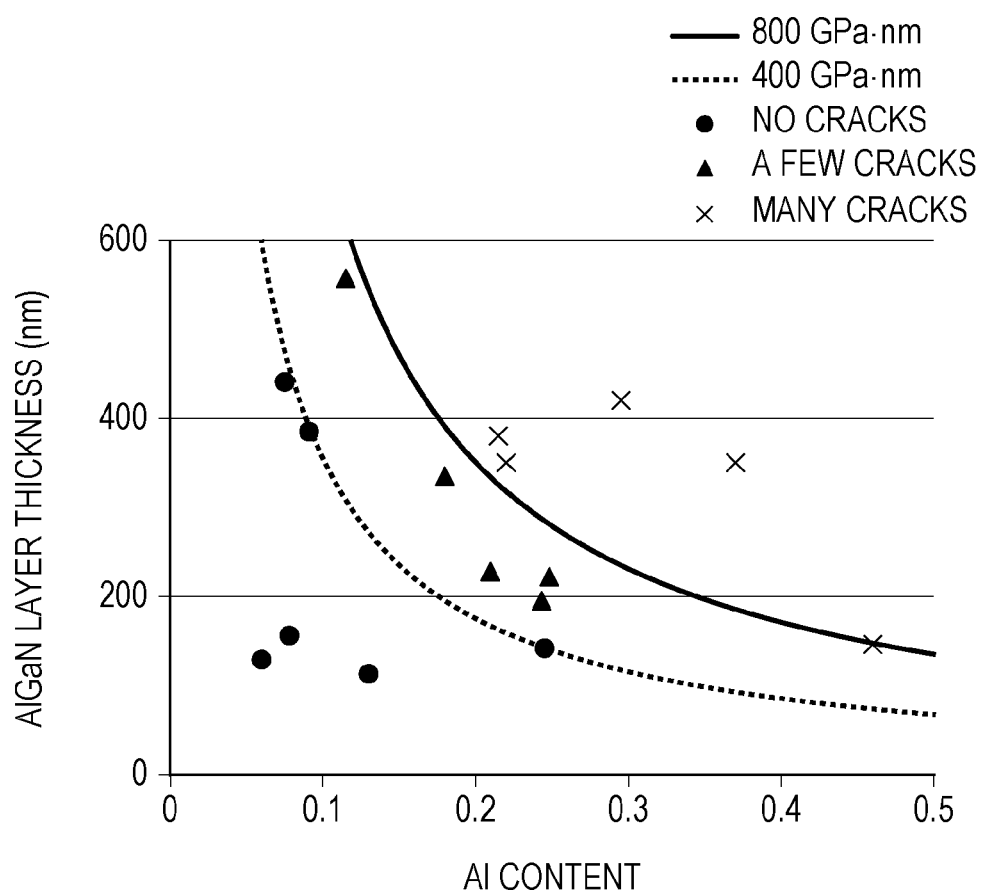
FIG. 3 is a graph showing the relationship between a combination of in-plane stress and layer thickness and occurrence of cracking.

FIG. 3 shows the relationship between a combination of the thickness of an AlGaN layer and the Al content in the AlGaN layer and occurrence of cracking in the AlGaN layer, the AlGaN layer being formed on a GaN template substrate formed by growing GaN on a few millimeters-square GaN substrate or a 2-inch sapphire substrate. Occurrence of cracking was evaluated by observing the surface of the AlGaN layer with a microscope. As is understood from FIG. 3, the higher the Al content, the larger the in-plane stress.

In FIG. 3, a combination of the thickness and the Al content at which cracking did not occur in the AlGaN layer is marked with a circle, a combination of the thickness and the Al content at which a few cracks were present in the AlGaN layer is marked with a triangle, and a combination of the thickness and the Al content at which a large number of cracks were present in a high density in the AlGaN layer is marked with a cross. In the AlGaN layers corresponding to the combinations marked with a cross, a reduction in lattice strain due to cracks formed in a high density was confirmed by X-ray diffraction reciprocal space mapping or curvature monitoring. On the other hand, in the AlGaN layers corresponding to the combinations marked with a triangle, a reduction in lattice strain was not confirmed by X-ray diffraction reciprocal space mapping or curvature monitoring.

In FIG. 3, the calculated critical layer thicknesses are shown by the solid line and the dotted line for which the products of the tensile stress (GPa) occurring in the AlGaN layer and the thickness (nm) of the AlGaN layer are 800 GPa·nm and 400 GPa·nm, respectively.

The experimental results shown in FIG. 3 shows the following: when the product of the tensile stress and the thickness exceeded 800 GPa·nm, cracking occurred in the AlGaN layer in a high density due to a tensile stress; and, when the product of the tensile stress and the thickness was 400 to 800 GPa·nm, cracking occurred in an small amount. Accordingly, in the semiconductor DBR according to the embodiment, the cumulative stress calculated using Formula (3) is preferably 800 GPa·nm or less and more preferably 400 GPa·nm or less.

Pitting caused by in-plane stress was examined by observing the surface of an InGaN layer having an In content of 5% which was grown on a GaN substrate using a microscope. As a result, it was confirmed that pitting occurred in a high density when the cumulative stress was negatively larger than −1,000 GPa·nm. It was also confirmed that pitting did not occur or occurred in a small amount when the cumulative stress was −1,000 GPa·nm or more and −600 GPa·nm or less. When the cumulative stress was larger than −600 GPa·nm and 0 GPa·nm or less, pitting did not occur. Accordingly, in the semiconductor DBR according to the embodiment, the cumulative stress calculated using Formula (3) is preferably −1,000 GPa·nm or more and more preferably −600 GPa·nm or more.

In order to utilize the semiconductor DBR 110 as a DBR and to set the cumulative stress to be within the range of −1,000 GPa·nm or more and 800 GPa·nm or less, the thicknesses of the layers constituting the semiconductor DBR 110 may be increased or reduced by 30% from the thicknesses corresponding to the above-described optical thicknesses. Note that the thicknesses of the layers constituting the semiconductor DBR according to the embodiment may deviate from the designed thicknesses by an amount on the order of the manufacturing error, which is also within the scope of the present invention.

EXAMPLES

Example 1

A nitride semiconductor DBR prepared in Example 1 is described below.

Figure 4:
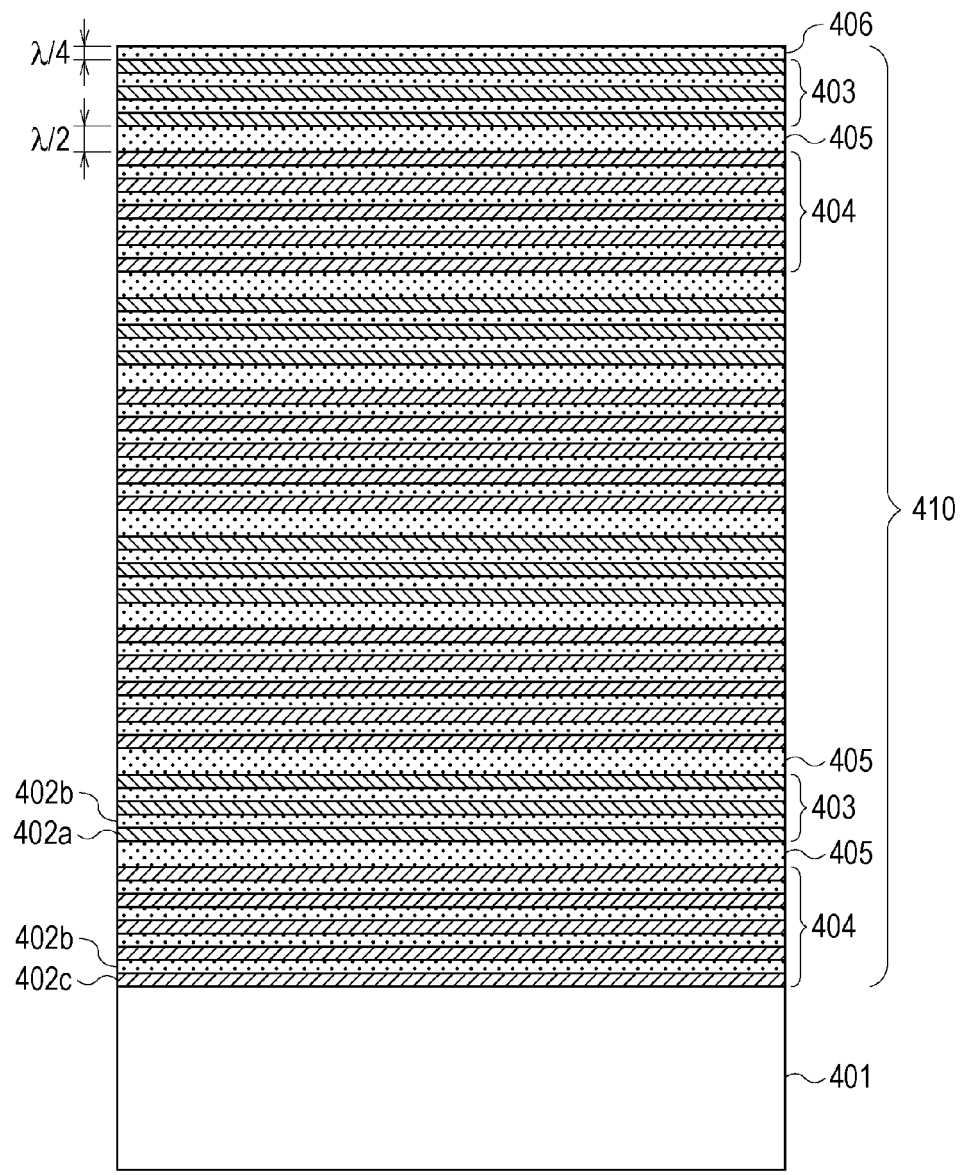
FIG. 4 is a diagram illustrating a nitride semiconductor DBR prepared in Example 1.

FIG. 4 is a schematic cross-sectional view of a nitride semiconductor DBR 410 formed on a GaN substrate 401. In Example 1, the nitride semiconductor DBR 410 was prepared by stacking an InGaN/GaN multilayer structure 404 that serves as a second multilayer structure, a GaN layer 405 that serves as a phase-matching layer, and an AlGaN/GaN multilayer structure 403 that serves as a first multilayer structure on top of one another repeatedly in this order. The nitride semiconductor DBR 410 of Example 1 was designed so that the peak reflectance occurs at a wavelength of 400 nm.

Table 2 shows the refractive index, the thickness corresponding to an optical thickness of $\lambda/4$ (for the phase-matching layer 405, the thickness corresponding to an optical thickness of $\lambda/2$), the designed thickness, the number of stacked layers, and the in-plane stress of each layer constituting the AlGaN/GaN multilayer structure 403, the InGaN/GaN multilayer structure 404, or the phase-matching layer 405.

TABLE 2

|  | InGaN/GaN multilayer structure | | AlGaN/GaN multilayer structure | | Phase-matching |
|---|---|---|---|---|---|
|  | $In_{0.05}Ga_{0.95}N$ layer | GaN layer | $Al_{0.30}Ga_{0.70}N$ layer | GaN layer | layer GaN layer |
| Refractive index | 2.61 | 2.54 | 2.42 | 2.54 | 2.54 |
| Thickness (nm) corresponding to $\lambda/4$ | 38.2 | 39.4 | 41.3 | 39.4 | 78.7* |
| Designed thickness (nm) | 40 | 40 | 36 | 40 | 80 |
| Number of stacked layers | 5 | 4 | 3 | 2 | 1 |
| In-plane stress (GPa) | −2.394982 | 0 | 3.2440392 | 0 | 0 |

The value marked with * denotes the thickness of the phase-matching layer which corresponds to an optical thickness of $\lambda/2$ In Example 1, the In content in the InGaN layer was set to 5%, and the Al content in the AlGaN layer was set to 30%. The thickness of the AlGaN layer was reduced by about 10% from the thickness corresponding to an optical thickness of $\lambda/4$ so that the tensile stress caused by the AlGaN layer was reduced.

A method for preparing the nitride semiconductor DBR 410 in Example 1 is described below.

A GaN substrate 401 was placed in an MOCVD system.

The temperature was increased to 900° C., and an InGaN layer 402c and a GaN layer 402b were alternately stacked on top of one another by epitaxial growth. Thus, an InGaN/GaN multilayer structure 404 was formed on the GaN substrate 401. The InGaN/GaN multilayer structure 404 includes five InGaN layers 402c and four GaN layers 402b. The InGaN/GaN multilayer structure 404 was formed using trimethylgallium (TMGa) and trimethylindium (TMIn) as raw materials by opening and shutting a valve supplying a TMIn raw material at 900° C.

While the substrate temperature was kept at 900° C., a GaN layer 405 that serves as a phase-matching layer was formed on the InGaN/GaN multilayer structure 404 by epitaxial growth. The GaN layer 405 was formed using only TMGa as a raw material.

The temperature was increased to 1,150° C., and an AlGaN layer 402a and a GaN layer 402b were alternately stacked on top of one another by epitaxial growth. Thus, an AlGaN/GaN multilayer structure 403 was formed on the GaN layer 405. The AlGaN/GaN multilayer structure 403 includes three AlGaN layers 402a and two GaN layers 402b. The AlGaN/GaN multilayer structure 403 was formed using TMGa and trimethylaluminium (TMAl) as raw materials by opening and shutting a valve supplying a TMAl raw material at 1,150° C.

While the substrate temperature was kept at 1,150° C., a GaN layer 405 that serves as a phase-matching layer was formed on the AlGaN/GaN multilayer structure 403.

Through the same steps as described below, the InGaN/GaN multilayer structure 404 and the AlGaN/GaN multilayer structure 403 were alternately formed on top of one another repeatedly with the GaN layers 405 each interposed between the corresponding pair of the InGaN/GaN multilayer structure 404 and the AlGaN/GaN multilayer structure 403. The nitride semiconductor DBR 410 prepared in Example 1 includes four InGaN/GaN multilayer structures 404 and four AlGaN/GaN multilayer structures 403.

With consideration of the phase of a standing wave, a GaN layer 406 having a thickness of 40 nm was formed on the AlGaN/GaN multilayer structure 403. The nitride semiconductor DBR 410 prepared in Example 1 includes the GaN layer 406 and thereby serves as a DBR.

The nitride semiconductor DBR 410 was prepared through the steps described above. The surface of the semiconductor DBR 410 was observed, and pits and cracks were not present.

Figure 5:
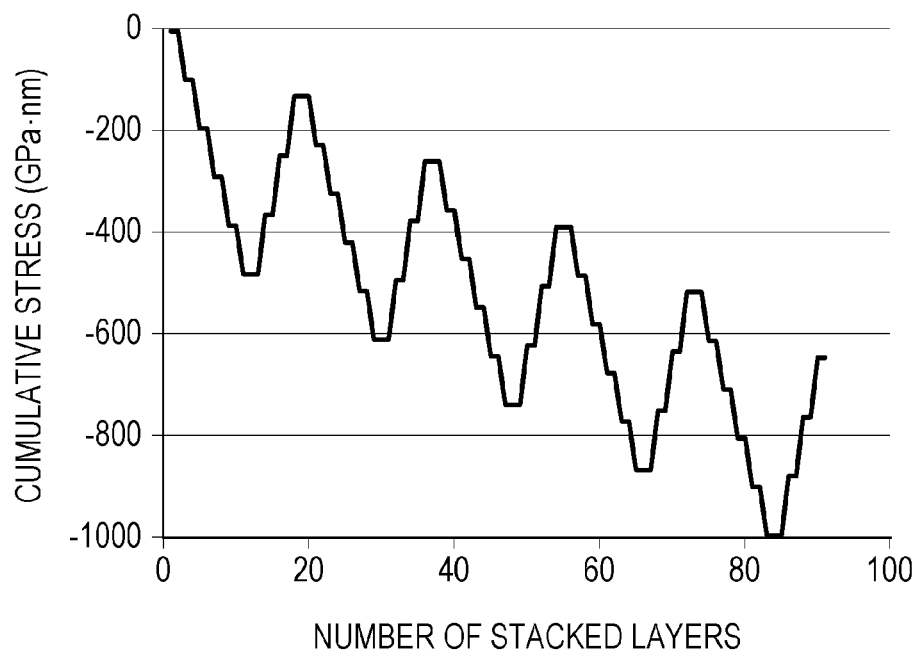
FIG. 5 is a graph showing the cumulative stress of a nitride semiconductor DBR prepared in Example 1.

FIG. 5 shows the cumulative stress calculated using Formula (3) which occurred during growth of the above-descried layers. In Example 1, the cumulative stress of the nitride semiconductor DBR 410 was designed to be within the range of −1,000 to 0 GPa·nm.

Figure 6:
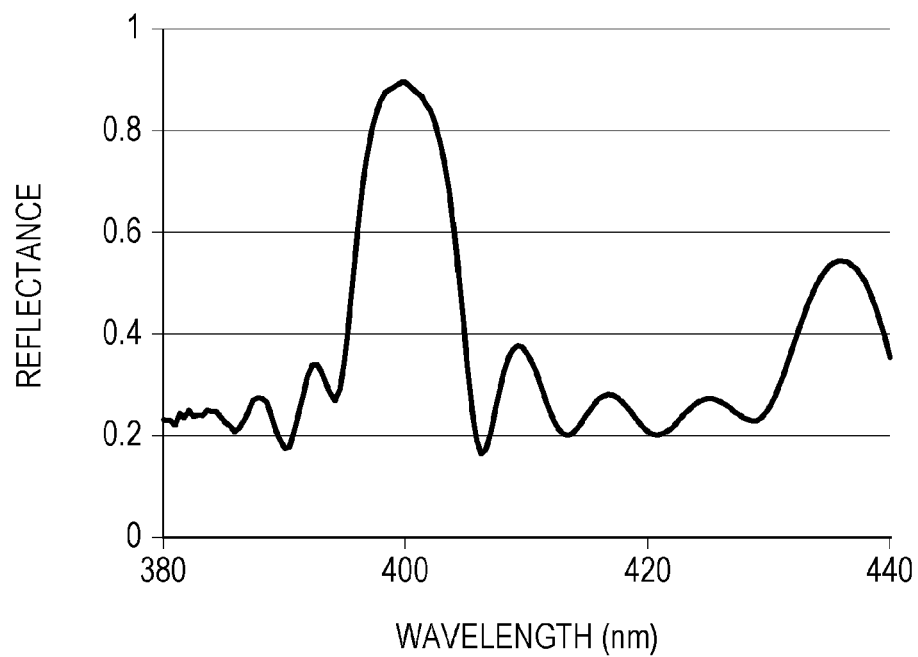
FIG. 6 is a graph showing a reflection property of a nitride semiconductor DBR prepared in Example 1.

FIG. 6 shows the reflection property of the nitride semiconductor DBR 410. The nitride semiconductor DBR 410 had the peak reflectance of 89% at a wavelength of 399 nm.

Example 2

In Example 2, a resonant-cavity light emitting diode (RC-LED) is described as an example of a semiconductor light-emitting device including a nitride semiconductor DBR.

Figure 7:
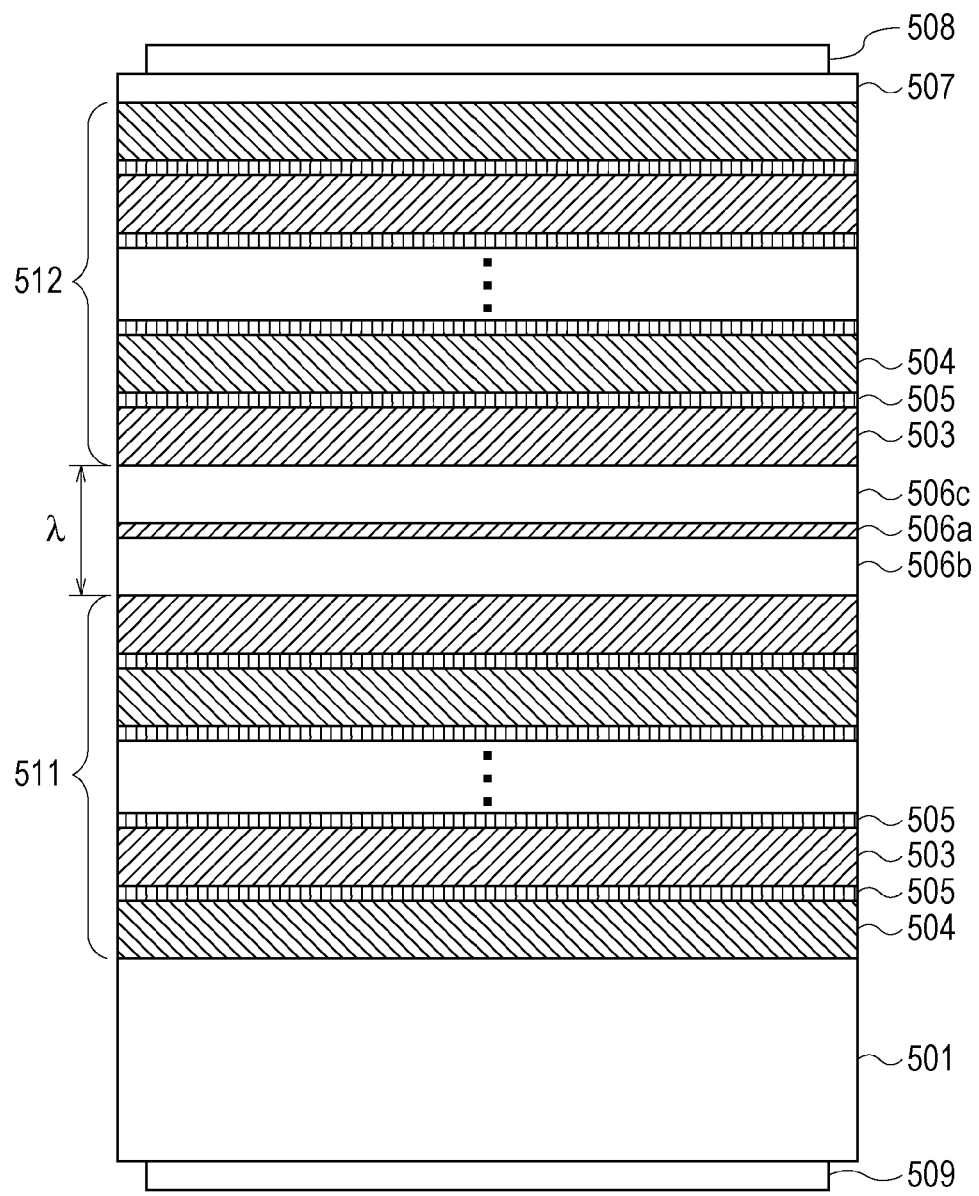
FIG. 7 is a diagram illustrating the structure of an RC-LED prepared in Example 2.

FIG. 7 is a schematic cross-sectional view of the RC-LED prepared in Example 2. The RC-LED of Example 2 includes a GaN substrate 501, a lower DBR 511, an active layer 506a, and an upper DBR 512, which are stacked on top of one another in this order. The active layer 506a is interposed between two reflectors, that is, the lower DBR 511 and the upper DBR 512, and thereby a cavity is formed. The lower DBR 511 and the upper DBR 512 were designed so that the peak reflectance occurs at a wavelength $\lambda$ of 400 nm.

The active layer 506a is constituted by an InGaN/GaN multiple quantum well and emits light when a carrier is injected into the active layer 506a.

The lower DBR 511 and the upper DBR 512 each include AlGaN/GaN multilayer structures 503, InGaN/GaN multilayer structures 504, and phase-matching layers 505.

Table 3 shows the refractive index, the thickness corresponding to an optical thickness of $\lambda/4$ (for the phase-matching layer 505, the thickness corresponding to an optical thickness of λ/2), the designed thickness, the number of stacked layers, the in-plane stress of each layer constituting the AlGaN/GaN multilayer structure 503, the InGaN/GaN multilayer structure 504, or the phase-matching layer 505.

doped with Mg. Through the above-described steps, the p-type upper DBR 512 with a reflectance of 95% was formed.

A p-type GaN layer 507 that serves as a contact layer was formed on the upper DBR 512. The thickness of the p-type GaN layer 507 was set to 10 nm.

TABLE 3

|  | InGaN/GaN multilayer structure | | AlGaN/GaN multilayer structure | | Phase-matching |
| --- | --- | --- | --- | --- | --- |
|  | $In_{0.05}Ga_{0.95}N$ layer | GaN layer | $Al_{0.20}Ga_{0.80}N$ layer | GaN layer | layer GaN layer |
| Refractive index | 2.61 | 2.54 | 2.46 | 2.54 | 2.54 |
| Thickness (nm) corresponding to λ/4 | 38.2 | 39.4 | 40.6 | 39.4 | 78.7* |
| Designed thickness (nm) | 40 | 40 | 39 | 40 | 80 |
| Number of stacked layers | 5 | 4 | 6 | 5 | 1 |
| In-plane stress (GPa) | −2.394982 | 0 | 2.1367086 | 0 | 0 |

The value marked with * denotes the thickness of the phase-matching layer which corresponds to an optical thickness of λ/2

In Example 2, the In content in the InGaN layer was set to 5%, and the Al content in the AlGaN layer was set to 20%.

A method for preparing the RC-LED in Example 2 is described below.

A GaN substrate 501 was placed in an MOCVD system.

The lower DBR 511 was formed on the GaN substrate 501 by stacking five InGaN/GaN multilayer structures 504 and five AlGaN/GaN multilayer structures 503 alternately with the GaN layers 505, which serve as phase-matching layers, each interposed between the corresponding pair of the InGaN/GaN multilayer structure 504 and the AlGaN/GaN multilayer structure 503 as in Example 1. Thus, the lower DBR 511 includes the InGaN/GaN multilayer structure 504, the GaN layer 505, and the AlGaN/GaN multilayer structure 503, which are stacked on top of one another repeatedly in this order. The semiconductors constituting the lower DBR 511 were doped with Si. Through the above-described steps, the n-type lower DBR 511 was formed.

A GaN layer 506b that serves as a spacer layer was formed on the lower DBR 511 at 1,150° C. An active layer 506a constituted by an InGaN/GaN multiple quantum well was stacked on the GaN layer 506b at 850° C. so that a GaN layer was positioned at the uppermost surface of the active layer 506a. A GaN layer 506c that serves as a spacer layer was formed on the active layer 506a at 1,150° C. The total optical thickness of the active layer 506a and the two spacer layers was set to λ (400 nm). The position of the active layer 506a was determined in accordance with the position of the resonance peak of a standing wave. Note that the total optical thickness of the active layer 506a and the two spacer layers is not limited to λ and may be set to any integer multiple of λ.

An upper DBR 512 was formed on the GaN layer 506c by stacking five AlGaN/GaN multilayer structures 503 and five InGaN/GaN multilayer structures 504 alternately with GaN layers 505, which serve as phase-matching layers, each interposed between the corresponding pair of the AlGaN/GaN multilayer structure 503 and the InGaN/GaN multilayer structure 504 in an order reverse to the order in the lower DBR 511. Thus, the upper DBR 512 includes the AlGaN/GaN multilayer structure 503, the GaN layer 505, and the InGaN/GaN multilayer structure 504, which are stacked on top of one another repeatedly in this order. The semiconductor layers constituting the upper DBR 512 were A p-type Ni/Au electrode 508 that serves as a contact electrode used for energization was formed on the p-type GaN layer 507. An n-type Ti/Al electrode 509 that serves as a contact electrode used for energization was formed on the GaN substrate 501.

The RC-LED of Example 2, which is an example of a semiconductor light-emitting device, was prepared as described above. Since the lower DBR 511 and the upper DBR 512 prepared in Example 2 are composed of AlGaN, InGaN, and GaN, they have high electric conductivities. Therefore, a carrier can be injected from the p-type electrode 508 and the n-type electrode 509 into the active layer 506a with efficiency.

Figure 8:
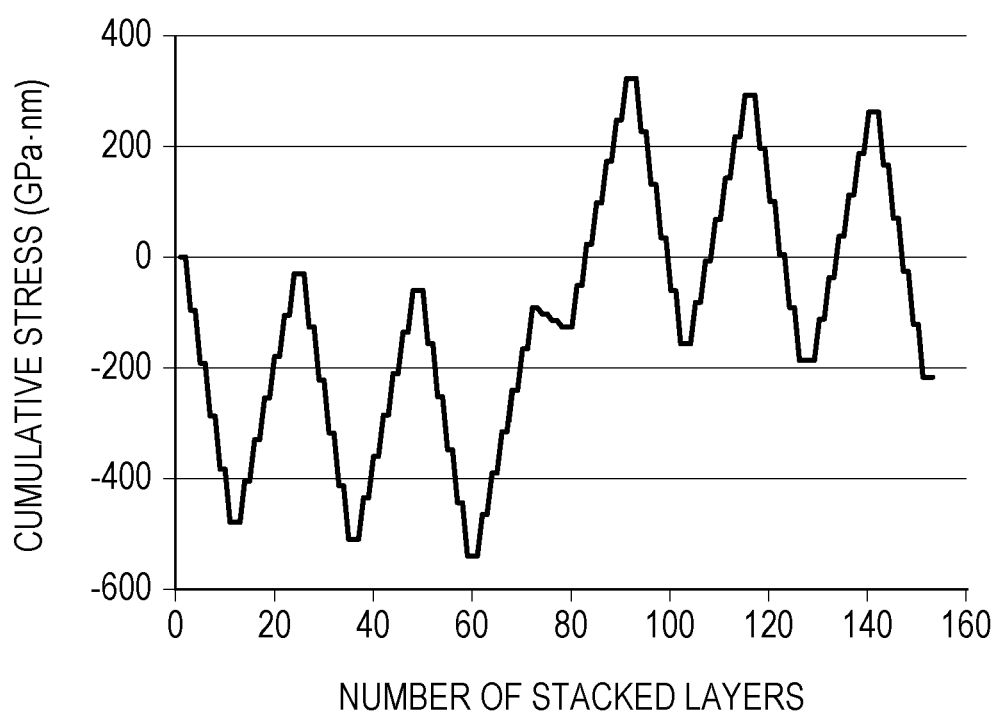
FIG. 8 is a graph showing the cumulative stress of an RC-LED prepared in Example 2.

FIG. 8 shows the cumulative stress calculated using Formula (3) which occurred during formation of a multi-layer of the RC-LED of Example 2. As is understood from FIG. 8, the cumulative stress of the RC-LED of Example 2 was designed so as to be within the range of −500 GPa·nm or more and 350 GPa·nm or less.

Example 3

In Example 3, a VCSEL is described as an example of a semiconductor light-emitting device including a nitride semiconductor DBR.

Figure 9:
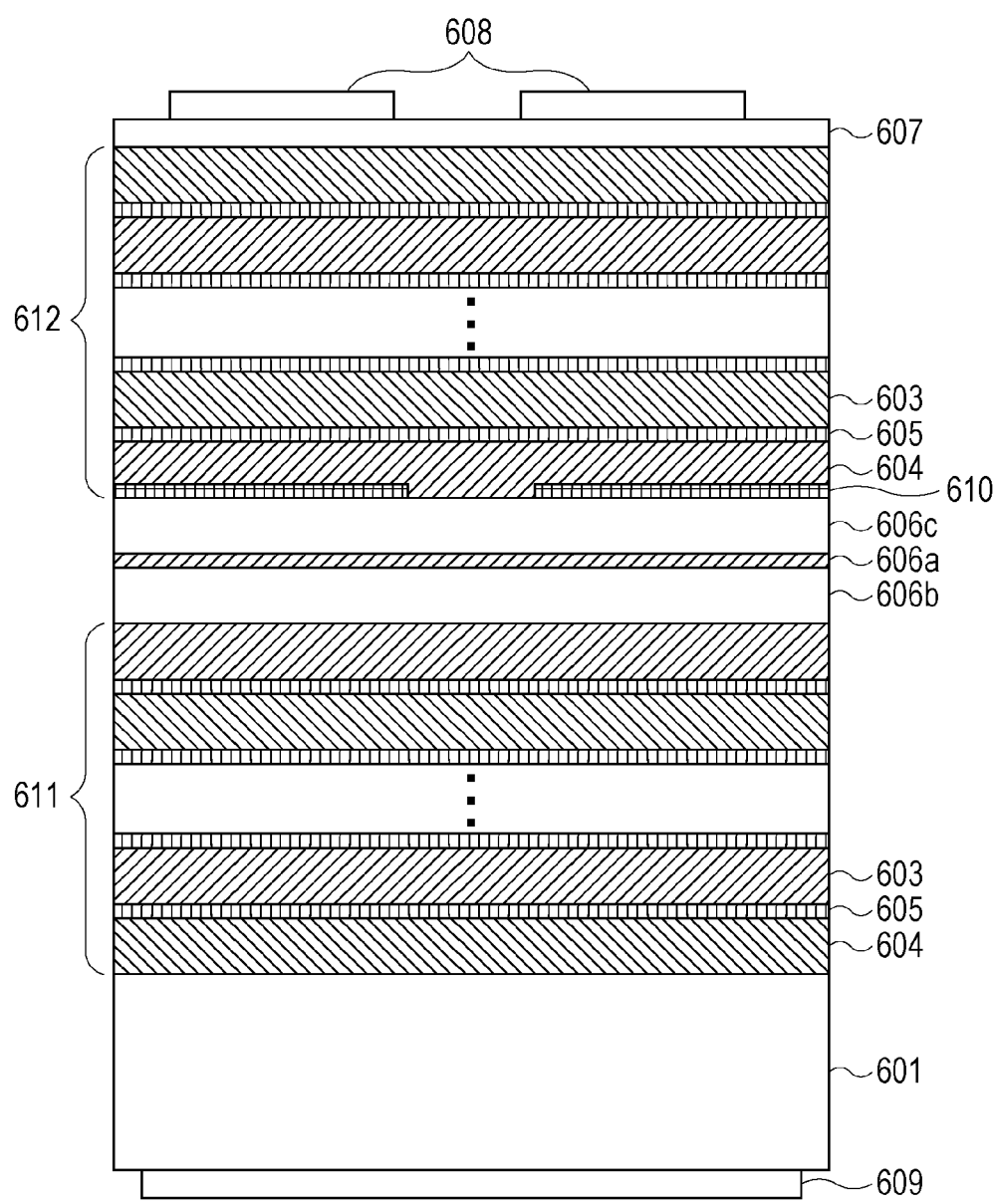
FIG. 9 is a diagram illustrating the structure of a VCSEL prepared in Example 3.

FIG. 9 is a schematic cross-sectional view of a VCSEL prepared in Example 3. In Example 3, a lower DBR 611 and an upper DBR 612 are disposed so as to face each other across an active layer 606a, and thereby a cavity is formed. The lower DBR 611 and the upper DBR 612 were designed so that a reflectance of 99% or more was achieved with light having a wavelength of 400 nm.

The active layer 606a is constituted by an InGaN/GaN multiple quantum well and emits light when a carrier is injected into the active layer 606a.

The lower DBR 611 and the upper DBR 612 each include AlGaN/GaN multilayer structures 603, InGaN/GaN multilayer structures 604, and phase-matching layers 605.

Table 4 shows the refractive index, the thickness corresponding to an optical thickness of λ/4 (for the phase-matching layer 605, the thickness corresponding to an optical thickness of λ/2), the designed thickness, the number of stacked layers, the in-plane stress of each layer constituting the AlGaN/GaN multilayer structure 603, the InGaN/GaN multilayer structure 604, or the phase-matching layer 605.

GaN multilayer structure 603 and the InGaN/GaN multilayer structure 604 in an order reverse to the order in the lower DBR 611. Thus, the upper DBR 612 includes the

TABLE 4

|  | InGaN/GaN multilayer structure | | AlGaN/GaN multilayer structure | | Phase-matching |
|---|---|---|---|---|---|
|  | $In_{0.05}Ga_{0.95}N$ layer | GaN layer | $Al_{0.35}Ga_{0.65}N$ layer | GaN layer | layer GaN layer |
| Refractive index | 2.61 | 2.54 | 2.40 | 2.54 | 2.54 |
| Thickness (nm) corresponding to $\lambda/4$ | 38.2 | 39.4 | 41.7 | 39.4 | 78.7* |
| Designed thickness (nm) | 40 | 40 | 41 | 40 | 80 |
| Number of stacked layers | 5 | 4 | 3 | 2 | 1 |
| In-plane stress (GPa) | −2.394982 | 0 | 3.807529 | 0 | 0 |

The value marked with * denotes the thickness of the phase-matching layer which corresponds to an optical thickness of $\lambda/2$.

In Example 3, the In content in the InGaN layer was set to 5%, and the Al content in the AlGaN layer was set to 35%.

A method for preparing the VCSEL in Example 3 is described below.

A GaN substrate 601 was placed in an MOCVD system.

A lower DBR 611 was formed on the GaN substrate 601 by, as in Example 1, stacking ten InGaN/GaN multilayer structures 604 and ten AlGaN/GaN multilayer structures 603 alternately with GaN layers 605, which serve as phase-matching layers, each interposed between the corresponding pair of the InGaN/GaN multilayer structure 604 and the AlGaN/GaN multilayer structure 603. Thus, the lower DBR 611 includes the InGaN/GaN multilayer structure 604, the GaN layer 605, and the AlGaN/GaN multilayer structure 603, which are stacked on top of one another repeatedly in this order. Semiconductors constituting the lower DBR 611 were doped with Si. Through the above-described steps, the n-type lower DBR 611 having a reflectance of 99.5% or more was prepared.

A GaN layer 606b that serves as a spacer layer was formed on the lower DBR 611 at 1,150° C. An active layer 606a constituted by an InGaN/GaN multiple quantum well was stacked on the GaN layer 606b at 850° C. so that a GaN layer was positioned at the uppermost surface of the active layer 606a. A GaN layer 606c that serves as a spacer layer was formed on the active layer 606a at 1,150° C. The total optical thickness of the active layer 606a and the two spacer layers was set to 400 nm. The position of the active layer 606a was determined in accordance with the position at which the resonance peak of a standing wave occurs. The total optical thickness of the active layer 606a and the two spacer layers is not limited to 400 nm and may be any integer multiple of 400 nm.

An AlN layer 610 having a thickness of 10 nm was formed on the GaN layer 606c. An aperture having a diameter of 10 μm was formed in the AlN layer 610 by photolithography and dry etching. The AlN layer 610 having an aperture serves as a current confinement layer. In Example 3, since the thickness of the AlN layer 610 is incomparably smaller than the diameter of the aperture, the AlN layer 610 would hardly affect a layer to be formed on the AlN layer 610.

An upper DBR 612 was formed on the GaN layer 606b by stacking eight AlGaN/GaN multilayer structures 603 and eight InGaN/GaN multilayer structures 604 alternately with GaN layers 605, which serve as phase-matching layers, each interposed between the corresponding pair of the AlGaN/ AlGaN/GaN multilayer structure 603, the GaN layer 605, and the InGaN/GaN multilayer structure 604, which are stacked on top of one another repeatedly in this order. Semiconductor layers constituting the upper DBR 612 were doped with Mg. Through the above-described steps, the p-type upper DBR 612 having a reflectance of 99.3% was prepared.

A p-type GaN layer 607 that serves as a contact layer was formed on the upper DBR 612. The thickness of the p-type GaN layer 607 was set to 10 nm.

A p-type Ni/Au electrode 608 having an aperture, which serves as a contact electrode used for energization, was formed on the p-type GaN layer 607. An n-type Ti/Al electrode 609, which serves as a contact electrode used for energization, was formed on the GaN substrate 601.

Through the above-described steps, the VCSEL of Example 3 was prepared.

Since the lower DBR 611 and the upper DBR 612 prepared in Example 3 are composed of AlGaN, InGaN, and GaN, they have high electric conductivities. Therefore, a carrier can be injected from the p-type electrode 608 and the n-type electrode 609 into the active layer 606a with efficiency.

Figure 10:
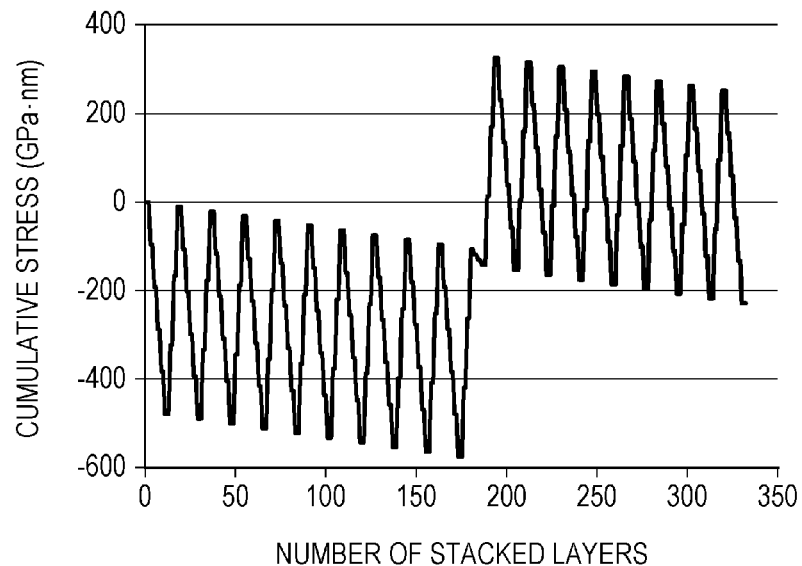
FIG. 10 is a graph showing the cumulative stress of a VCSEL prepared in Example 3.

FIG. 10 shows the cumulative stress calculated using Formula (3) which occurred during formation of a multilayer of the VCSEL of Example 3. According to FIG. 10, it is understood that the cumulative stress of the VCSEL of Example 3 was within the range of −600 to 350 GPa·nm.

Example 4

Figure 11:
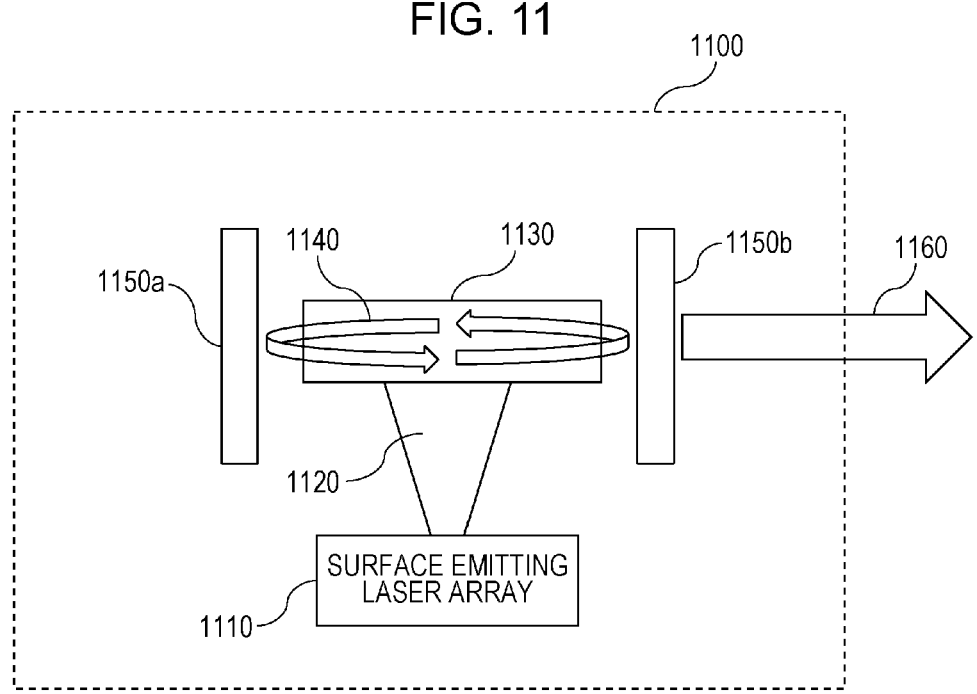
FIG. 11 is a schematic diagram illustrating a solid-state laser according to Example 4.

An example of a solid-state laser including a surface emitting laser array constituted by the VCSELs described in Example 3 which are arranged in the form of an array, the surface emitting laser array serving as an excitation light source, is described below with reference to FIG. 11. FIG. 11 is a schematic diagram illustrating the solid-state laser according to Example 4.

A solid-state laser 1100 according to Example 4 includes a surface emitting laser array 1110, a solid-state laser medium 1130, and two reflectors 1150a and 1150b.

The surface emitting laser array 1110 emits excitation light 1120 having a wavelength of λ toward the solid-state laser medium 1130. Upon absorbing the excitation light 1120, the solid-state laser medium 1130 emits light 1140 due to laser transition. The light 1140 emitted from the solid-state laser medium 1130 is repeatedly reflected by the two reflectors 1150a and 1150b, and consequently the solid-state laser is brought into the oscillation state. Thus, the solid-state laser 1100 in the oscillation state emits a solid laser beam 1160 that has transmitted through the reflector 1150b.

The wavelength λ of the excitation light 1120 emitted from the surface emitting laser array 1110 is preferably determined in accordance with the absorption spectrum of the solid-state laser medium 1130. In other words, a wavelength at which the peak reflectance of the semiconductor DBR used in the surface emitting laser array 1110 occurs is preferably determined in accordance with the absorption spectrum of the solid-state laser medium 1130. More preferably, the semiconductor DBR is designed so that the peak reflectance of the semiconductor DBR occurs in the vicinity of a wavelength at which the peak absorption spectrum of the solid-state laser medium 1130 occurs. For example, in the case where an alexandrite crystal is used as a solid-state laser medium 1130, efficient oscillation of the solid-state laser may be realized by setting a wavelength λ at which the peak reflectance of the semiconductor DBR occurs to 400 nm, which is a wavelength close to the peak absorption spectrum of an alexandrite crystal.

Any solid-state laser medium may be employed for the solid-state laser according to Example 4.

Example 5

Figure 12:
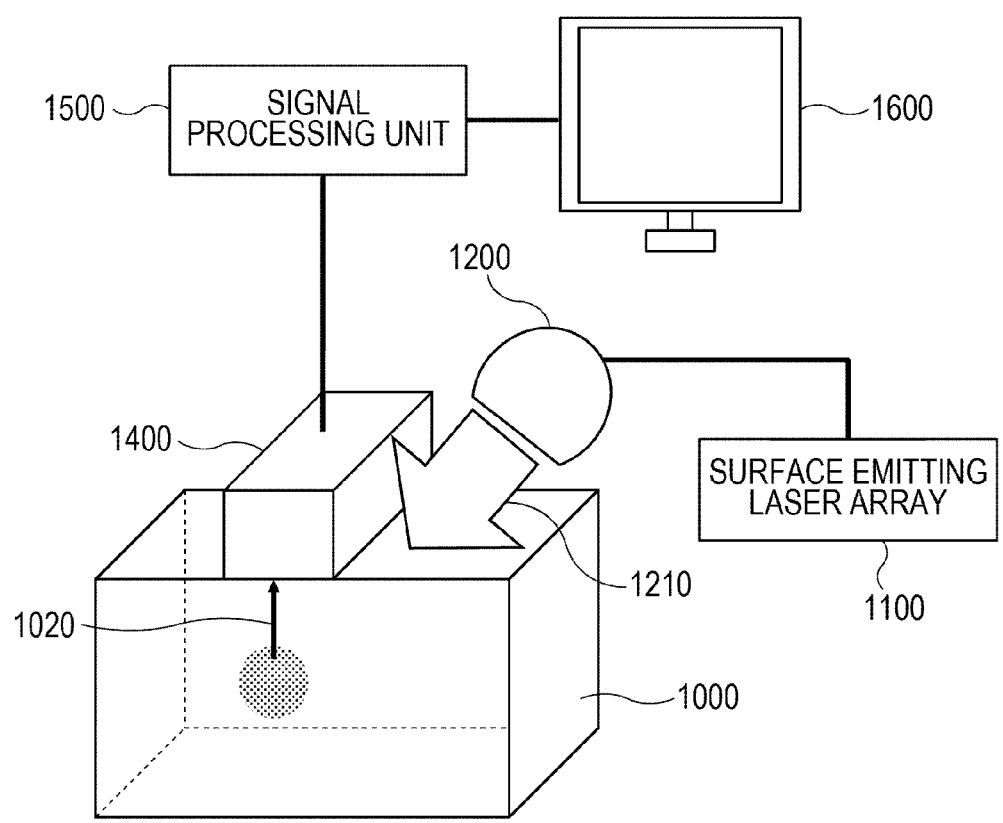
FIG. 12 is a schematic diagram illustrating a photoacoustic apparatus according to Example 5.

A photoacoustic apparatus including the solid-state laser 1100 described in Example 4 is described with reference to FIG. 12.

The photoacoustic apparatus according to Example 5 includes a solid-state laser 1100, an optical system 1200, a probe 1400, a signal processing unit 1500, and a displaying unit 1600.

Light emitted by the solid-state laser 1100 is transformed into pulsed light 1210 through the optical system 1200, and the pulsed light 1210 impinges on an analyte 1000. Thereby, a photoacoustic wave 1020 is generated inside the analyte 1000 due to a photoacoustic effect. The probe 1400 detects the photoacoustic wave 1020 that has propagated through the analyte 1000 and receives a time-series electric signal. On the basis of the time-series electric signal, the signal processing unit 1500 obtains information about the inside of the analyte and displays the information about the inside of the analyte on the displaying unit 1600.

In Example 5, the wavelength of light emitted by the solid-state laser 1100 is desirably set so that light having the wavelength can propagate to the inside of the analyte 1000. Specifically, when the analyte 1000 is a living body, a suitable wavelength may be 500 nm or more and 1,200 nm or less. In order to determine the distribution of the optical characteristic value of a tissue of a living body which is positioned in the relatively vicinity of the surface of the living body, for example, light having a wavelength within the range of 400 to 1,600 nm, which is wider than the range of the above-described suitable wavelength, may also be used.

Examples of the analyte information according to Example 5 include the initial sound pressure of a photoacoustic wave, light energy absorption density, absorption factor, and the concentration of a substance constituting the analyte. The concentration of a substance is, for example, an oxygen saturation, an oxyhemoglobin concentration, a deoxyhemoglobin concentration, and a total hemoglobin concentration. The total hemoglobin concentration is a sum of an oxyhemoglobin concentration and a deoxyhemoglobin concentration. In Example 5, the analyte information may not necessarily be numeric data and may be information about positional distribution in the analyte. Specifically, the analyte information may be distribution information such as information about the distribution of absorption factor or about the distribution of oxygen saturation.

Example 6

Figure 13A:
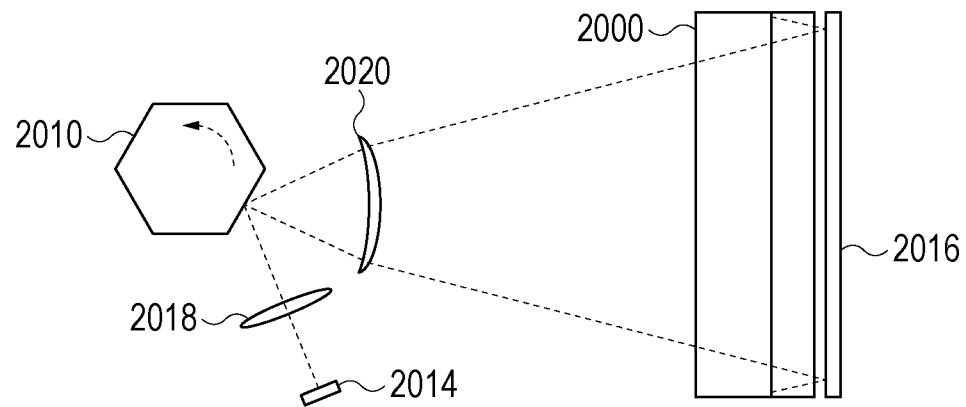
FIGS. 13A and 13B are schematic diagrams illustrating an image-forming apparatus according to Example 6.
Figure 13B:
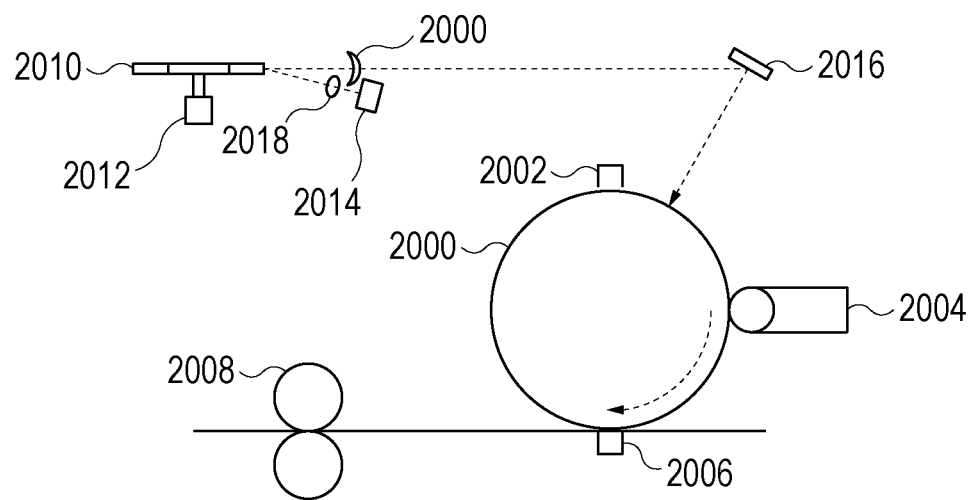

With reference to FIGS. 13A and 13B, an example of an image-forming apparatus including a surface emitting laser array that serves as a light source, the surface emitting laser array being constituted by the VCSELs described in Example 3 which are arranged in the form of an array.

FIGS. 13A and 13B are a plan view and a side view of the image-forming apparatus according to Example 6, respectively.

In FIGS. 13A and 13B, the reference numeral 2000 denotes a photosensitive drum (photosensitive member), the reference numeral 2002 denotes a charge unit, the reference numeral 2004 denotes a development unit, the reference numeral 2006 denotes a transfer charge unit, the reference numeral 2008 denotes a fix unit, the reference numeral 2010 denotes a rotary polygon mirror, and the reference numeral 2012 denotes a motor.

The reference numeral 2014 denotes a surface emitting laser array, the reference numeral 2016 denotes a reflector, the reference numeral 2018 denotes a collimator lens, and the reference numeral 2020 denotes a f-θ lens.

In Example 6, the rotary polygon mirror is rotated by the motor 2012 shown in FIG. 13B.

The surface emitting laser array 2014 serves as a light source used for recording. The surface emitting laser array 2014 is configured to emit light by a laser driver (not shown) on the basis of an image signal.

Thus, an optically modulated laser beam is emitted from the surface emitting laser array 2014 toward the rotary polygon mirror 2010 through the collimator lens 2018.

The rotary polygon mirror 2010 rotates in the direction of the arrow. The laser beam emitted from the surface emitting laser array 2014 is reflected by the rotary polygon mirror 2010 and transformed into a deflected beam whose reflection angle is continuously changed at the reflection surface due to the rotation of the rotary polygon mirror 2010.

The reflected light is corrected in terms of distortion aberration and the like through the f-θ lens 2020 and impinges on the photosensitive drum 2000 via the reflector 2016. The photosensitive drum 2000 is scanned with the light in the main scanning direction. Due to beam light reflected by a surface of the rotary polygon mirror 2010, an image formed of a plurality of lines corresponding to the surface emitting laser array 2014 is formed on the photosensitive drum 2000 in its main scanning direction.

The photosensitive drum 2000, which has been charged in advance by the charge unit 2002, is sequentially exposed to light by being scanned with the laser beam, and thereby an electrostatic latent image is formed.

The photosensitive drum 2000 rotates in the direction of the arrow. The electrostatic latent image is developed using the development unit 2004. The resulting visible image is transferred onto transfer paper using a transfer charge unit 2006.

The transfer paper, on which the visible image is transferred, is transported to the fix unit 2008 to fix the image on the transfer paper and then ejected from the image-forming apparatus.

In Examples 4, 5, and 6 described above, examples of an apparatus including the surface emitting laser array according to an embodiment of the present invention are described. However, the types of apparatus to which the surface emitting laser array can be applied are not limited to the above-described apparatuses.

According to the present invention, a semiconductor DBR including layers having good crystal quality can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-128283, filed Jun. 19, 2013, which is hereby incorporated by reference herein in its entirety.

What is claimed is:

1. A semiconductor distributed Bragg reflector (DBR) comprising:
a first multilayer structure including
a plurality of first semiconductor layers and
one or more second semiconductor layers each interposed between a corresponding pair of the plurality of first semiconductor layers;
a second multilayer structure including
a plurality of third semiconductor layers and
one or more second semiconductor layers each interposed between a corresponding pair of the plurality of third semiconductor layers; and
a protection layer interposed between the first multilayer structure and the second multilayer structure,
wherein,
the second semiconductor layer has a lower decomposition temperature than the first semiconductor layer,
the third semiconductor layer has a lower decomposition temperature than the second semiconductor layer,
the semiconductor DBR has a peak reflectance at a wavelength $\lambda$,
the plurality of first semiconductor layers, the one or more second semiconductor layers, and the plurality of third semiconductor layers each have an optical thickness of $n\lambda/4$, where n is an odd number of 1 or more,
the protection layer has an optical thickness of $m\lambda/2$, where m is a natural number of 1 or more, and
a portion of the protection layer at which the protection layer is brought into contact with the second multilayer structure includes a material having a higher decomposition temperature than the third semiconductor layer,
wherein a conductivity type of the first multilayer structure and a conductivity type of the second multilayer structure are the same as each other.

2. The semiconductor DBR according to claim 1, wherein,
the second semiconductor layer has a higher refractive index than the first semiconductor layer, and
the third semiconductor layer has a higher refractive index than the second semiconductor layer.

3. The semiconductor DBR according to claim 1, wherein the material having a higher decomposition temperature than the third semiconductor layer is the same as a material constituting the second semiconductor layer.

4. The semiconductor DBR according to claim 1, wherein a material constituting the protection layer is the same as the material constituting the second semiconductor layer.

5. The semiconductor DBR according to claim 1, wherein,
the first semiconductor layer includes AlGaN,
the second semiconductor layer includes GaN, and
the third semiconductor layer includes InGaN.

6. The semiconductor DBR according to claim 1 including the first multilayer structure, the protection layer, the second multilayer structure, and the protection layer that are stacked repeatedly in order.

7. A light-emitting device comprising:
two reflectors; and
an active layer between the two reflectors,
wherein at least one of the two reflectors is the semiconductor DBR according to claim 1.

8. A solid-state laser comprising:
the light-emitting device according to claim 7; and
a solid-state laser medium that is excited by light emitted from the light-emitting device.

9. A photoacoustic apparatus comprising:
the solid-state laser according to claim 8;
a probe that outputs an electric signal upon detecting a photoacoustic wave generated from an analyte irradiated with light emitted from the solid-state laser; and
a signal processing unit that obtains information about the inside of the analyte on the basis of the electric signal.

10. An image-forming apparatus comprising:
the light-emitting device according to claim 7; and
a photosensitive member that is exposed to light emitted from the light-emitting device.

11. A semiconductor DBR comprising:
a first semiconductor layer;
a second semiconductor layer having a lower decomposition temperature than the first semiconductor layer; and
a third semiconductor layer having a lower decomposition temperature than the second semiconductor layer,
wherein,
a portion of the semiconductor DBR has a structure in which the third semiconductor layer, the second semiconductor layer, the third semiconductor layer, the second semiconductor layer, the first semiconductor layer, the second semiconductor layer, and the first semiconductor layer are stacked in order,
in the structure, the thickness of the second semiconductor layer interposed between the third semiconductor layers is different from the thickness of the second semiconductor layer interposed between the first semiconductor layer and third semiconductor layer, and
in the structure, the thickness of the second semiconductor layer interposed between the first semiconductor layers is different from the thickness of the second semiconductor layer interposed between the first semiconductor layer and third semiconductor layer,
wherein a conductivity type of the first multilayer structure and a conductivity type of the second multilayer structure are the same as each other.

12. The semiconductor DBR according to claim 11, wherein,
the second semiconductor layer interposed between the third semiconductor layers has an optical thickness of $n\lambda/4$, where n is an odd number of 1 or more,
the second semiconductor layer interposed between the first semiconductor layers has an optical thickness of $n\lambda/4$, where n is an odd number of 1 or more, and the second semiconductor layer interposed between the first semiconductor layer and third semiconductor layer has an optical thickness of $m\lambda/2$, where m is a natural number of 1 or more.

13. The semiconductor DBR according to claim 12, wherein the first semiconductor layer and the third semiconductor layer have an optical thickness of $n\lambda/4$, where n is an odd number of 1 or more.

14. The semiconductor DBR according to claim 11, wherein, the second semiconductor layer has a larger refractive index than the first semiconductor layer, and the third semiconductor layer has a larger refractive index than the second semiconductor layer.

15. The semiconductor DBR according to claim 11, wherein, the first semiconductor layer includes AlGaN, the second semiconductor layer includes GaN, and the third semiconductor layer includes InGaN.

\* \* \* \* \*